United States Patent [19]

Tanagho et al.

[11] Patent Number: 5,656,478
[45] Date of Patent: Aug. 12, 1997

[54] SMOOTH MUSCLE TISSUE FORMATION IN VIVO USING CULTURED SMOOTH MUSCLE CELLS COMBINED WITH AN EXTRACELLULAR MATRIX

[75] Inventors: Emil A. Tanagho, San Rafael; Rajvir Dahiya, San Carlos; Tom F. Lue, Hillsborough; Gerald R. Cunha, Foster City, all of Calif.

[73] Assignee: The Regents of the University of California, Oakland, Calif.

[21] Appl. No.: 201,850

[22] Filed: Feb. 25, 1994

[51] Int. Cl.$^6$ .............................. C12N 5/00; C12N 5/08
[52] U.S. Cl. ..................... 435/378; 435/402; 435/395; 424/93.7
[58] Field of Search ....................... 435/240.2, 240.23, 435/240.243; 424/93.7; 530/356, 350, 353, 399

[56] References Cited

PUBLICATIONS

Shoemaker, W.C., et al., "The Experimental Use of Seromuscular Grafts In Bladder Reconstruction: Preliminary Report," *The Journal of Urology* 73(2):314–321 (Feb. 1955).

Novick, A.C., et al., "Experimental Bladder Substitution Using a Biodegradable Graft of Natural Tissue," *Journal of Biomedical Materials Research*, 12:125–147 (1978).

Norris, M.A., et al., "Bladder Reconstruction In Rabbits With Glutaraldehyde–Stabilized Amniotic Membranes," *Urology*, 19(6):631–635 (Jun. 1982).

Tachibana, M., et al., "Ureteral Replacement Using Collagen Sponge Tube Grafts," *The Journal of Urology*, 133(5):866–869 (1985).

Fishman, I.J., et al., "Use of Fresh Placental Membranes For Bladder Reconstruction," *The Journal of Urology*, 138(11):1291–1294 (Nov. 1987).

Scott, R., et al., "The Evolution of a Biodegradable Membrane for Use in Urology Surgery," *British Journal of Urology*, 62:26–31 (1988).

Cartwright, P.C., et al., "Bladder Autoaugmentation: Partial Detrusor Excision to Augment the Bladder Without Use of Bowel" *The Journal of Urology* 142:1050–1053 (Oct. 1989).

Weingarten, J.L., et al., "Augmentation Myoperitoneocystoplasty," *The Journal of Urology*, 144(7):156–158 (Jul. 1990).

Pippi Salle, J.L., et al., "Seromuscular Enterocystoplasty in Dogs," *The Journal of Urology*, 144:454–456 (Aug. 1990).

Sandusky, Jr., G.E., et al., "Histologic Findings After In Vivo Placement of Small Intestine Submocosal Vascular Grafts and Saphenous Vein Grafts in the Carotid Artery in Dogs," *American Journal of Pathology*, 140(2):317–324 (Feb. 1992).

Meezan, E., et al., "A Simple, Versatile, Nondisruptive Method for the Isolation of Morphologically and Chemically Pure Basement Membranes from Several Tissues," *Life Sciences*, 17(11):1721–1732 (Dec. 1, 1975).

Birukov, K.G., et al., "Synthesis and Epxression of Smooth Muscle Phenotype Markers in Primary Culture of Rabbit Aortic Smooth Muscle Cells: Influence of Seeding Density and Media and Relation to Cell Contractility," *Experimental Cell Research*, 204:46–53 (1993).

Campbell, J.H., et al., "Methods of Growing Vascular Smooth Muscle in Culture," In Campbell JH, and Campbell GR (eds): *Vascular Smooth Muscle in Culture*, Chapter 2, vol. 1, Boca Raton, FL: CRC Press, (1987).

Cunha, G.R., et al., "Role of Epithelial–Mesenchymal Interactions in the Differentiation and Spatial Organization of Visceral Smooth Muscle," *Epithelial Cell Biology*, 1:76–83 (1992).

Blondell, et al., "Heart Cells in Culture: A Simple Method for Increasing the Proportion of Myoblasts," *Experientia*, 27(3):356–358 (1971).

McDonagh, et al., "Highly enriched Preparations of Cultured Myocardial Cells for Biochemical and Physiological Analyses," *J. of Molecular and Cellular Cardiology*, 19:785–793 (1987).

Li et al., J. Am. Soc. Nephrol., 4(3):516 (1993).

Pauly et al., Circulation, 86(6):68–73 (1992).

Hunek et al, Connect. Tissue Res., 8(3–4) pp. 181–184 (1981).

*Primary Examiner*—John W. Rollins
*Assistant Examiner*—Kristin K. Larson
*Attorney, Agent, or Firm*—Townsend and Townsend and Crew

[57] ABSTRACT

The present invention provides a method of growing smooth muscle cells in a host with the purpose of maintaining natural cellular function by the function of smooth muscle tissue. In this method, smooth muscle cells are freed from isolated smooth muscle tissue then cultured and injected into the host in combination with an extracellular matrix.

9 Claims, 1 Drawing Sheet

SMOOTH MUSCLE TISSUE FORMATION IN VIVO USING CULTURED SMOOTH MUSCLE CELLS COMBINED WITH AN EXTRACELLULAR MATRIX

This invention was made with Government support under Grant No. 5RO1NS18029-12, awarded by the National Institutes of Health. The Government has certain rights in this invention.

BACKGROUND OF THE INVENTION

Replacement of tissue in a patient is known in a variety of contexts. These include bone replacement, removal and replacement of fat tissue for breast, buttock or penis enhancement, and the injection of collagen for the removal of wrinkles. In the latter case, bovine collagen is typically used which leads to allergic reactions in some patients.

The present invention relates to a method of growing smooth muscle cells in a host with the purpose of maintaining natural cellular function to replace lost or damaged smooth muscle tissue. This method utilizes human muscle tissue wherein the smooth muscle cells are isolated, cultured, then reinjected in areas where there is deficient muscle tissue. This method can be carried out using a patient's own muscle tissue so as to avoid the possibility of immunological responses, or the cells may be isolated from fetal tissue.

This method will be particularly useful where cultured smooth muscle tissue can be injected around a bladder neck and the proximal urethra to provide functional integrity to the segment and to restore sphincteric function.

SUMMARY OF THE INVENTION

This invention provides a method of growing smooth muscle cells in a host with the purpose of maintaining natural cellular function to reproduce lost or damaged smooth muscle tissue. This method uses the following steps;

(a) isolating smooth muscle tissue and freeing smooth muscle cells from the isolated tissue;

(b) culturing the smooth muscle cells; and (c) injecting into the host the smooth muscle cells of step (b) in combination with an extracellular matrix.

In a preferred embodiment the method uses enzymatic digestion to free said smooth muscle cells from the isolated tissue. The smooth muscle tissue is preferably xenographic, allographic or autographic, most preferably autographic. In other preferred embodiments the smooth muscle tissue is tissue from either the bladder, uterus, intestine, seminal vesicle or prostate.

In other preferred embodiments, the smooth muscle cells are isolated by a process of differential adhesion. In still other preferred embodiments, the extracellular matrix consists of collagen or elastin or a combination of collagen and elastin. In still further preferred embodiments, the host is a mammal, most preferably a human.

This invention further provides a method of enriching smooth muscle cells in a mixture by differential adhesion. This method uses the steps;

(a) isolating a mammalian tissue sample comprising smooth muscle cells, epithelial cells, fibroblastic cells and extracellular matrix;

(b) digesting the matrix to free the cells of step (a) into a suspension;

(c) culturing the suspension in sequential steps whereby the fibroblastic cells adhere to a solid support faster than epithelial cells or smooth muscle cells and isolating a supernatant containing the smooth muscle cells and the epithelial cells; and (d) culturing said supernatant whereby the smooth muscle cells adhere to a solid support and removing the epithelial cells.

In a preferred embodiment, the solid support of step (d) is a plastic growth support. In another preferred embodiment, step (b) uses enzymatic digestion to separate the cells from the extracellular matrix. In yet another preferred embodiment, the mammalian tissue sample is human.

BRIEF DESCRIPTION OF THE DRAWINGS

FIG. 1a shows a view of a guinea pig seminal vesicle showing the epithelium, lamina proprium and thick smooth muscle layer. FIG. 1b shows the pure smooth muscle which remains after removal of the epithelium and lamina proprium. FIG. 1c shows the smooth muscle graft which has maintained its smooth muscle differentiation.

DETAILED DESCRIPTION

Figure 1A:
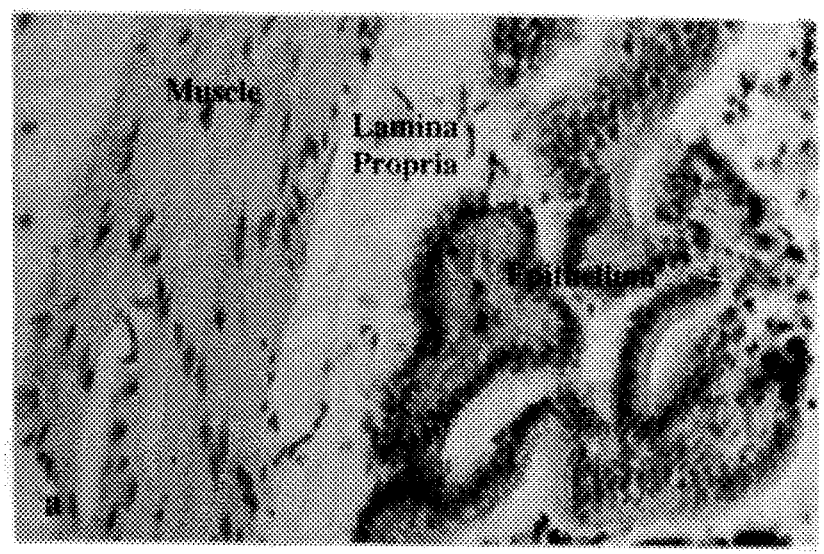
FIGS. 1A–1C show that smooth muscle differentiation is maintained when smooth muscle is grafted in the renal capsule of nude mice.

The following abbreviations are used herein: DMEM, Dulbecco's modified Eagle's medium; RPMI, Roswell Park Memorial Institute medium; HBSS, Hank's Balanced Salt Solution; FCS, fetal calf serum; EGF, epidermal growth factor; TGF-β, β-transforming growth factor; DMSO, dimethylsulfoxide;

As used herein the term "allographic tissue" refers to tissue which is isolated from an individual and used in another individual of the same species. The term "xenographic tissue" refers to tissue which is isolated from an individual of one species and placed in an individual of another species. The term "autographic tissue" refers to tissue isolated from an individual which is grafted back into that individual.

As used herein, the term "differential adhesion" refers to the process of enriching the amount of a particular cell type in a mixture by culturing the cells for a period of time sufficient for one type of cell to adhere to a solid support such that the adherent cells can be removed from the mixture. This process can be repeated until the desired cells are either isolated by virtue of their attachment to the solid support or until the mixture contains predominantly the desired cells.

The term "enzymatic digestion" refers to the degradation of tissues using enzymes such as trypsin and collagenase. Typically, enzymatic digestion will be used to isolate smooth muscle cells from tissue.

As used herein, the term "extracellular matrix" refers to any non-cellular matrix, typically composed of proteins and glycoproteins which surrounds cells. Examples of extracellular matrices include connective tissue and cartilage.

The term "host" refers to an animal which is the recipient of tissue which has been purified, cultured and transplanted from another species (the donor) or from itself.

As used herein, the term "natural cellular function" refers to the function which particular cells provide in vivo. For example, the natural cellular function of smooth muscle cells includes contraction which is responsible for movement of food along the gut, of blood along some contractile vessels, and sphincteric function around the bladder and urethra.

The term "solid support" refers to the flasks, growth chambers and growth supports for the cell cultures which are typically glass or plastic.

The present invention is a method of growing smooth muscle cells in a host with the purpose of maintaining natural cellular function to reproduce lost or damaged smooth muscle tissue. In this method, smooth muscle tissue is first isolated and smooth muscle cells are freed from the tissue. The smooth muscle cells are then cultured and injected into the host in combination with an extracellular matrix.

Isolation of Smooth Muscle Tissue

The methods and conditions for isolating smooth muscle cells from tissue is well known to one of skill in the art. Variations of the typical methods are largely due to the age and species of the donor, the purpose for which the tissue is being isolated and the particular preferences of the investigators. For general methods, see Freshney, *Culture of Animal Cells: A Manual of Basic Technique*, AR Liss Inc., New York (1987), incorporated herein by reference.

The tissue used in the present inventive method can be obtained from a variety of sources including human, rabbit, rat, pig and chick sources. When the source of tissue is human, it can be isolated from either adult individuals or from fetal sources. More particularly, smooth muscle tissue will be surgical tissue from aortas, arteries, the bladder, uterus, intestine or prostate.

Once the tissue has been isolated, it will be digested by mechanical and/or enzymatic methods to free the smooth muscle cells.

A. Elastic arteries

When the tissue being used is elastic (i.e. aortas, typically rabbit, rat or pig), the dissected aortas will typically be placed in cold balanced salt solution containing fetal calf serum. Connective tissue and fat will be removed by dissection under microscope and the vessels will be cut longitudinally. The intima and the inner two thirds of the media is removed in strips from the adventitia and transferred to a flask containing collagenase. After digestion for a suitable period of time, the collagenase will be removed and replaced with a solution containing elastase. Additional collagenase will then be added and the tissue stirred until all tissue has completely dispersed into single cells.

B. Muscular arteries

When muscular arteries such as caudal arteries are to be used, the vessels are first manually cleaned of fat and connective tissue. The remaining tissue is placed in collagenase and stirred gently at 37°C. At approximately 10 minute intervals the adventitia is pipetted away until only the translucent muscle layer remains. This tissue is then placed in fresh collagenase, cut into strips and transferred to a flask containing growth medium and incubated overnight at 37°C. Following the incubation, the tissue suspension is centrifuged and the supernatant is discarded. The tissue is taken up in trypsin-versene solution and stirred until the cells are completely dissociated. The addition of FCS inactivates the trypsin and the suspension is again centrifuged to provide a pellet of cells.

C. Mesenteric vessels

When mesenteric vessels are used, the large amounts of fat must be removed by first placing the tissue in cold HBSS (to make the tissue firm) and then transferring the tissue to a collagenase solution. After 10 minutes the tissue is transferred back to cold HBSS, and the fat and connective tissue is stripped away. Fat globules are removed by continuous replacement of the cold HBSS. The mesenteric arterioles and artery are removed from the vein and its branches, then the arterioles are separated form the artery. The arterioles are placed in collagenase and the adventitia is gently pipetted away. The remaining muscle layer is transferred to fresh collagenase and carried on as described for muscular arteries.

D. Embryonic blood vessels, Bladder, Uterus, and Colon tissue

The vessels from embryonic and neonatal tissue, as well as tissue from the bladder, uterus and colon can be dispersed into cells by successive incubations with collagenase and 0.1% trypsin in calcium and magnesium free HBSS.

In a preferred embodiment, the excised tissue is first placed in a salt solution, typically Hank's Balanced Salt Solution (HBSS) or phosphate saline buffer, and blood is removed with subsequent washing. The tissue is then defatted using sterile scissors and transferred to another vessel containing a growth medium supplemented with antibiotics, growth stimulants, and antifungal agents. The basic growth medium is not critical, however Dulbecco's Modified Eagle Medium (DMEM) or RPMI are preferred. The tissue is minced with sterile forceps and scissors then digested with trypsin. Following the trypsinization, the supernatant is discarded and the remaining pellet is digested with collagenase and hyaluronidase to degrade any extracellular matrix. After digestion, the samples are centrifuged. Centrifugation will typically be carried out at from about 3000 to about 8000 rpm, preferably about 5000 rpm. The length of time for centrifugation is generally of from about 7 to 13 minutes, with about 10 minutes being preferred. Following centrifugation, the supernatant is discarded and the pellet is resuspended in growth medium. The amount of smooth muscle cells in a mixture can also be enriched prior to culturing the cells.

The present invention also provides a method for the enriching smooth muscle cells in a mixture by differential adhesion. This method involves first isolating a mammalian tissue sample, preferably human, which contains smooth muscle cells, fibroblastic cells, epithelial cells and extracellular matrix. The extracellular matrix is then removed to provide a suspension of cells which is cultured such that the fibroblastic cells adhere to a solid support faster or in greater numbers for a given period of time than either the epithelial cells or the smooth muscle cells. The supernatant, containing the epithelial cells and the smooth muscle cells, is drawn off and cultured for a period of time sufficient for the smooth muscle cells to adhere to a solid support. The supernatant, containing the epithelial cells, is drawn off leaving a solid support with primarily smooth muscle cells attached. These cells may be removed by trypsinization. In certain preferred embodiments, the solid support is a plastic growth support such as a plastic petri dish. In other preferred embodiments, the extracellular matrix is removed from the tissue sample using enzymatic digestion.

Once the appropriate mixture of smooth muscle cells is obtained, the mixture can be cultured and immortalized. Pellets of the resulting immortalized culture can then be injected with an extracellular matrix and will grow and survive as smooth muscle tissue.

Primary Culture

Techniques and methods for establishing a primary culture of smooth muscle cells are also well known to those of skill in the art and are generally disclosed in Ricciardelli, et al., *In Vitro Cell Dev. Biol.* 25:1016–1024 (1989), incorporated herein by reference. Variations in growth media, use of sera, media supplements, culture chambers and substrates are typically determined empirically depending on the particular cells being cultured and the use for which the cells were harvested.

The growth medium for primary cell culture will typically be a buffered salt solution containing amino acids, vitamins and other nutrients including serum or a serum-substitute. Examples of such growth media are DMEM and RPMI. Additionally, the medium will contain other supplements to enhance cell growth and prevent the death of the culture.

Buffered salt solutions are designed either to equilibrate with atmospheric conditions or to equilibrate with a gas phase containing 5 to 10% carbon dioxide. In the present inventive methods, solutions of the latter type are preferred. These media are based on Earle's salts and are buffered with a bicarbonate/carbonic acid system which maintains the pH in a $CO_2$ equilibrated incubator. Particularly preferred media are Dulbecco's Modified Eagle Medium (DMEM) and RPMI.

The addition of serum to a growth medium provides a source of growth factors. However, a number of drawbacks are associated with the use of serum including lot-to-lot variability and the unpredictable effects of serum constituents. As a result, culture conditions have been defined which reduce or eliminate the requirement for serum. These alternative conditions include the use of serum replacements, supplemented sera and media supplements. In the present inventive method, the growth medium will typically contain of from 5 to 15% fetal calf serum, preferably about 10% fetal calf serum. Additionally, the fetal calf serum will be heat-inactivated in such a manner to inactivate any proteases while maintaining the viability of the desired growth factors.

As noted, media supplements are added to reduce the serum supplementation. Such supplements typically contain growth promoting additives such as insulin, transferrin, trace elements (such as manganese, molybdenum, vanadium, nickel, or tin), ascorbic acid, non-essential amino acids, L-glutamine and other growth factors. Other additives to the growth medium include antibiotics and antifungal agents. Typically, broad spectrum antibiotics such as penicillin, streptomycin, neomycin and polymyxin are used. Preferred are penicillin and streptomycin. Preferred antifungal agents are fungizone and nystatin. Particularly preferred is fungizone.

The culture chambers and substrates for vascular smooth muscle cells are generally plastic culture dishes or flasks. However, smooth muscle cells will also grow on glass coverslips placed in plastic dishes and on a variety of membranes and fabrics including collagen membranes, elastic membranes, smooth silicone rubber substrata, polyacrylonitrile fabrics, dacron velour and Parylene-C coated polypropylene microfabric.

In a preferred embodiment, a primary culture of smooth muscle cells is established by suspending the pellet of initially isolated cells in complete DMEM (containing non-essential amino acids, L-glutamine, heat-inactivated FCS, penicillin, streptomycin, insulin, transferrin, ascorbic acid, EGF, trace element solution and fungizone). The suspension is placed in a 100 mm plastic plate and kept at 37° C. in a $CO_2$ humidified incubator. The amount of carbon dioxide will typically be about 4% to about 10%, with 7% being preferred. After 3 to 4 hours, the unattached cells are inoculated into petri dishes and grown for 7 to 10 days. The resulting monolayers are then subcultured by trypsinization.

The process of trypsinization to remove adherent cells from a culture surface is well known to those of skill in the art. Briefly, trypsin or trypsin.EDTA is solubilized in a $Ca^{++}$ and $Mg^{++}$ free buffered salt solution (i.e., HBSS) and the pH is adjusted to 7.4–7.6. Any media or serum is removed from the monolayer by washing with $Ca^{++}$ and $Mg^{++}$ free buffered salt solution. The trypsin solution is then added to the vessel containing the monolayer in sufficient quantity to cover the monolayer and the mixture is incubated for about 2 minutes at 37°C. The trypsin solution is removed from the vessel and the monolayer is again incubated until the cells detach from the surface. When this process is complete, serum or medium containing serum is added to the vessel to inhibit further trypsin activity which can damage the cells. These cells can be resuspended by gentle pipetting to break up any clumps, and diluted with media for cell counts and secondary culturing.

When the cultured cells will not be used immediately, they can be frozen in liquid nitrogen, then thawed and cultured to provide growing cells for further use.

Cell Freezing and Thawing

Smooth muscle cells are typically frozen to avoid loss by contamination and to provide a constant supply for future use.

To freeze cells, cultures are dissociated with trypsin to provide cell pellets which are suspended in complete medium containing either glycerol or dimethylsulfoxide as a cryopreservative. In a preferred embodiment, complete DMEM containing about 10% dimethylsulfoxide (DMSO) is used. Additionally, the medium will contain from 10 to 25% FCS, more preferably about 20% FCS. The cell pellet is suspended in the freezing medium at a concentration of about 1 to $5 \times 10^7$ cells/mL. Aliquots are placed into vials which are cooled to −20° C. for 2 hours and then transferred to a liquid nitrogen-containing storage vessel until further use.

Frozen cells are fragile and require gentle handling. Frozen cells should be thawed quickly and plated directly into complete growth media. Cells which are sensitive to the added cryopreservative (glycerol or DMSO) should be centrifuged, to remove the medium containing the preservative, and plated into complete growth medium. In a preferred embodiment, vials containing frozen cells are defrosted in a 37° C. water bath for one minute. The cells are transferred to a sterile centrifuge tube, complete DMEM is added, and the cells are centrifuged. The supernatant is discarded and the pellet is resuspended in complete DMEM and plated into 75 mm tissue culture flasks to establish a secondary culture.

Secondary Cultures

Secondary cultures can be obtained from previously frozen cells which had become confluent in the primary tissue culture dishes. Centrifugation of the thawed cells provides a pellet which is resuspended in complete DMEM, counted and plated in tissue culture flasks. Following incubation as described for the primary culture, the cells are washed with calcium and magnesium-free phosphate buffered saline solution and detached from the dishes by trypsinization. The cells are then counted and the appropriate portions are combined with an extracellular matrix prior to treatment of the host.

Injection of Cells with Extracellular Matrix

Normal attachment, growth and development of smooth muscle cells is dependent on a number of attachment factors. These factors are typically supplied in the form of an extracellular matrix. Depending on the components in the extracellular matrix, the attachment, cell spreading, growth, differentiation and motility of the cells can all be influenced. Typical extracellular matrices will include collagen, elastin, or laminin or a combination thereof. In addition to these proteins, the extracellular matrices will typically contain growth factors such as TGF-$\beta$, fibroblast growth factor and tissue plasminogen activator.

Injection of cells and extracellular matrix will typically be carried out either submucosally or subcapsularly. When it is desired to restore sphincteric function the smooth muscle cells will be injected around the bladder or anal sphincter, preferably in a three or four locations. The injections used in the present inventive method will typically contain about 10–20 million cells suspended in about 0.1 mL of growth medium. Each injection will also contain an equal volume of a solubilized extracellular matrix in a pharmaceutically acceptable carrier for a total volume of about 0.2 mL. Concentration ranges for the solubilized extracellular matrix in each injection will typically be about 2.0–20 mg/mL. Pharmaceutically acceptable carriers are well-known to those skilled in the art. The choice of carrier will be determined in part by the particular injection being made. Formulations suitable for submucosal and subcapsular injection include aqueous isotonic sterile injection solutions and sterile growth media. In a preferred embodiment, the extracellular matrix is a commercially available solubilized basement membrane preparation such as Matrigel™ which contains laminin, collagen IV, heparin sulfate proteoglycans, entactin, nidogen, and growth factors.

The progress of a particular treatment can be followed by endoscopic examination or by other urodynamic studies known to those of skill in the art. In instances in which one treatment is insufficient to grow smooth muscle cells or restore smooth muscle function, a repeat treatment can be administered.

Optionally, a treatment of smooth muscle cells will be accompanied by a treatment of antibiotics either by injection or oral dosage.

The following experimental results are offered by way of example and are not meant to limit the scope of the invention.

EXAMPLES

Example 1

This example illustrates the culture techniques for isolating and growing smooth muscle cells which can be used in the present inventive method.

PRIMARY CULTURES:

A small piece of surgical tissue (smooth muscle collagen, elastic, etc.) was excised and placed in 35 mm petri dish containing cold Hank's Balanced Salt Solution (HBSS). The blood was removed by washing with cold HBS solution and the tissue was defatted using a pair of sterile scissors. The tissue was transferred to another petri dish containing Dulbecco's modified Eagle's medium (DMEM), containing 1% (v/v) non-essential amino acids, 2 µM L-glutamine, 10% heat-inactivated fetal calf serum, penicillin (100 units/mL), streptomycin (100 µg/mL), insulin (5 µg/mL), transferrin (5 µg/mL), ascorbic acid (5 µg/mL), EGF (5 µg/mL), trace element solution (1 µl/mL), and fungizone (0–25 µg/mL), and minced into small pieces (1–2 mm) with a pair of sterile forceps and scissors. The tissue was trypsinized with 1.5 mg/mL of trypsin at 37° C. for 2 hrs. At the end of incubation, the supernatant which contained mainly epithelial cells was discarded and the pellet was digested with collagenase (200 to 250 units/mL) and hyaluronidase (112 units/mL) and gentle mechanical dissociation with a magnetic stir bar at 37° C. for 12 to 16 hrs. At the end of incubation most of the tissue was digested. These samples were centrifuged at 5,000 rpm for 10 minutes. The supernatant was discarded and the pellet was resuspended in the complete DMEM and cultured in 100 mm plate at 37° C. in a 7% $CO_2$ humidified incubator. After 3–4 hours, about 20–40% of the cells were attached on the plate. The unattached cells were then inoculated into three 100 mm plastic petri dishes. After 7–10 days, monolayers were subcultured by trypsinization.

VIABILITY OF CULTURES:

The viability of these cells was tested by using Trypan Blue Dye Exclusion method. The dye (2.5 mg/mL) was added to the aliquots of cell suspensions and incubated for 10 minutes at room temperature. The dead cells, which pick up the stain, were counted by hemacytometer and the percent viability was calculated.

SECONDARY CULTURES:

After the cells are confluent in 100 mm Falcon plastic tissue culture dishes, the cells were washed with calcium and magnesium-free phosphate buffered saline solution and detached from culture dishes by incubating for 3 minutes with a solution of trypsin (0.5 mg/mL) and EDTA (0.2 mg/mL). The cells were centrifuged at 5,000 rpm for 5 minutes, the supernatant was discarded, and the cell pellet was resuspended in complete DMEM. The cells were counted by using a Coulter Counter. About 50,000 cells were plated in each 150 mm plastic tissue culture flask. After 15 min, complete DMEM was added to each culture flask.

CELL FREEZING AND THAWING:

Cell freezing: Cultures were dissociated with trypsin as described above and the cell pellets were gently resuspended in freshly prepared 10% dimethylsulfoxide (DMSO), 20% fetal calf serum in complete DMEM. The resuspended cells were added to special vials, kept at –20° C. for 2 hrs, then transferred to liquid nitrogen until further use.

Cell thawing: Vials were defrosted in a water bath (37° C.) for about one minute. The vial exteriors were disinfected with 70% ethanol, and the cells were transferred to sterile 15 mL centrifuge tubes. About 5 mL of DMEM was added and the cells were centrifuged at 5,000 rpm for about 5 minutes. The supernatant was discarded and the pellet was resuspended in complete DMEM, transferred to 75 mm tissue culture flasks and allowed to grow to confluence before subculturing.

Example 2

This example illustrates the in vivo growth capacity of the cultured cells in nude mice.

Smooth muscle cells were cultured as described in Example 1. About 5–6 million cells were injected subcutaneously into the right and left posterior flank area of each mouse (3–4 week old male BALB/C "Nu/Nu" athymic mice, Simonsen Labs, Inc., Gilroy, Calif., USA). The cells were injected with and without Matrigel™ (0.1 mL, Becton Dickinson, Bedford, Mass., USA). Cell growth was measured with a caliper every week after their appearance. The graft volume was calculated as follows:

$$Volume=(Length \times Width^2)/2$$

Table A below shows the results of cell growth in mice after six weeks.

TABLE A

| Treatment | Smooth Muscle Cell Growth ($cm^3$) |
|---|---|
| Matrigel™ alone | No growth |
| Smooth muscle cells | 0.108 $cm^3$ |
| Smooth muscle cells and Matrigel™ | 0.25 $cm^3$ |

As the results in Table A indicate, Matrigel™ increases the growth of smooth muscle cells by 2–3 fold in nude mice.

Example 3

This example illustrates that the smooth muscle differentiation was maintained when smooth muscle tissue was grafted in the renal capsule of nude mice.

Figure 1B:
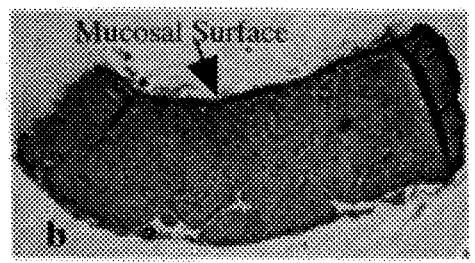
Figure 1C:
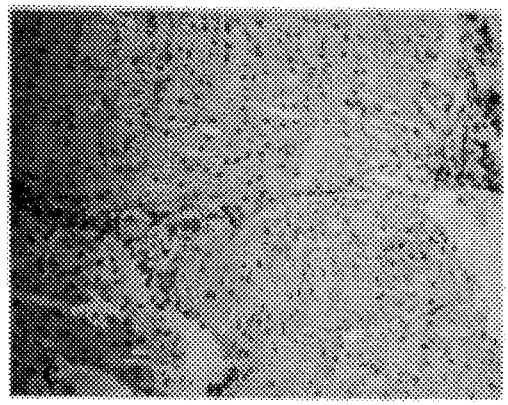

A seminal vesicle was excised from an adult guinea pig and is shown in transverse section in FIG. 1a. The mucosa and surrounding smooth muscle is apparent (using H & E stain). The gland was opened with a scalpel and the epithelial mucosa was removed by scraping with a scalpel. The resultant muscle sheath was examined to confirm the absence of epithelial contamination (FIG. 1b) using smooth muscle α-actin stain. A 1×1×2 mm piece of the smooth muscle sheath was grafted under the renal capsule of a nude mouse. After four weeks, the smooth muscle sheet has remained intact and has maintained its smooth muscle differentiation (FIG. 1c, with H & E stain).

Example 4

The example illustrates the method of enriching smooth muscle cells in a mixture of cells from guinea pig seminal vesicle using the process of differential adhesion.

The seminal vesicle from guinea pig was excised and placed in a 35 mm petri dish containing DMEM and opened longitudinally with a pair of sterile forceps and scissors. Blood and fat were removed by washing and gentle scraping and the tissue was transferred to another petri dish containing medium. The epithelial layer was scraped gently to remove most of the epithelial cells.

The remaining tissue was transferred to another petri dish containing complete DMEM as described in Example 1. The tissue was digested with collagenase (200–250 units/mL) and hyaluronidase (112 units/mL) and gentle mechanical dissociation with a magnetic stir bar at 37° C. for 5–6 hrs. The tissue was then washed with DMEM and trypsinized with 1.5 mg/mL of trypsin at 37° C. for 4–5 hr. At the end of incubation the tissue was almost completely digested. The digested samples were centrifuged at 5,000 rpm for 10 minutes and the supernatant was discarded. The pellet containing the cells was resuspended in complete DMEM and cultured in a 100 mm culture plate at 37° C. in a 7% $CO_2$ humidified incubator. The cell population was then partially purified by plating for 5–6 hr. During this time, fibroblastic cells attach to the plate, leaving the smooth muscle and epithelial cells in suspension. The cells in suspension were re-plated into a new culture flask. After about 12–24 hr the smooth muscle cells were attached. The majority of the epithelial cells, which attach more slowly than smooth muscle cells, were eliminated when the culture medium was replaced after 24 hrs. Any epithelial cells which had become attached to the culture flask were rapidly overgrown by smooth muscle cells. Upon subculture all remaining epithelial cells, if any, were eliminated, thus giving a pure smooth muscle cell population.

What is claimed is:

1. A method of growing smooth muscle tissue in a host, said method comprising;

(a) isolating smooth muscle cells from a smooth muscle tissue sample;

(b) culturing said smooth muscle cells; and (c) injecting into said host the smooth muscle cells of step (b) in combination with a solubilized basement membrane extracellular matrix comprising laminin, collagen IV, heparin sulfate proteoglycans, entactin, nidogen, and growth factors, such that natural cellular function of said injected smooth muscle cells is maintained allowing the smooth muscle cells to grow and proliferate, and smooth muscle tissue is formed.

2. The method of claim 1 wherein said smooth muscle cells of step (a) are isolated using enzymatic digestion.

3. The method of claim 1 wherein said smooth muscle tissue is xenographic.

4. The method of claim 1 wherein said smooth muscle tissue is allographic.

5. The method of claim 1 wherein said smooth muscle tissue is autographic.

6. The method of claim 1 wherein said smooth muscle tissue is selected from the group of tissues consisting of bladder tissue, uterine tissue, intestinal tissue, seminal vesicle and prostatic tissue.

7. The method of claim 1 wherein said smooth muscle cells of step (a) are isolated using differential adhesion.

8. The method of claim 1 wherein said host is a mammal.

9. The method of claim 1 wherein said host is a human.

* * * * *